US007951558B2

(12) United States Patent
Lee et al.

(10) Patent No.: US 7,951,558 B2
(45) Date of Patent: May 31, 2011

(54) METHOD FOR EXTRACELLULAR PRODUCTION OF TARGET PROTEINS BY CO-EXPRESSION OF OMPF AND TARGET PROTEINS

(75) Inventors: Sang Yup Lee, Daejeon (KR); Jong Hyun Choi, Daejeon (KR)

(73) Assignee: Korea Advanced Institute of Science and Technology (KR)

( * ) Notice: Subject to any disclaimer, the term of this patent is extended or adjusted under 35 U.S.C. 154(b) by 785 days.

(21) Appl. No.: 11/995,689

(22) PCT Filed: Jul. 15, 2005

(86) PCT No.: PCT/KR2005/002284
§ 371 (c)(1),
(2), (4) Date: Feb. 6, 2008

(87) PCT Pub. No.: WO2007/011077
PCT Pub. Date: Jan. 25, 2007

(65) Prior Publication Data
US 2008/0206814 A1    Aug. 28, 2008

(51) Int. Cl.
*C12P 21/06* (2006.01)
*C12N 15/00* (2006.01)
*C12N 1/20* (2006.01)
(52) U.S. Cl. .................. 435/69.1; 435/252.3; 435/320.1
(58) Field of Classification Search .................. 435/69.1, 435/320.1, 252.3
See application file for complete search history.

(56) References Cited

U.S. PATENT DOCUMENTS
5,958,754 A    9/1999    Wong et al.

FOREIGN PATENT DOCUMENTS
| JP | 2004521656 A | 7/2004 |
| KR | 20030014959 A | 2/2003 |
| WO | 2003016538 A1 | 2/2003 |

OTHER PUBLICATIONS

Abrahmsen, L., et al., "Abstract Only: Analysis of signals for secretion in the staphylococcal protein A gene", "Embo. Journal", 1985, pp. 3901-3906, vol. 4, No. 13B.
Aristidou, Aristos A., et al., "Abstract Only: Effects of glycine supplement on protein production and release in recombinant *Escherichia coli*", "Biotechnology Letters", Apr. 1993, pp. 331-336, vol. 15, No. 4.
Choi, J. H., et al., "Secretory and extracellular production of recombinant proteins using *Escherichia coli*", "Appl. Microbiol. Biotechnol.", 2004, pp. 625-635, vol. 64.
Choi, Jong Hyun, et al., "Production of recombinant proteins by high cell density culture of *Escherichia coli*", "Chemical Engineering Science", 2006, pp. 876-885, vol. 61.

Eugene, W., et al., "Abstract Only: TolAIIIu co-overexpression facilitates the recovery of periplasmic recombinant proteins into the . . .", "Protein Expression and Purification", Oct. 1998, pp. 13-22, vol. 14, No. 1.
Jeong, Ki Jun, et al., "Excretion of human beta-endorphin into culture medium by using outer membrane protein F as a fusion partner in . . .", "Applied and Environmental Microbiology", Oct. 2002, pp. 4979-4985, vol. 68, No. 10.
Jobling, Michael G., et al., "Abstract Only: Construction and characterization of versatile cloning vectors for efficient delivery of native . . .", "Plasmid", Nov. 1997, pp. 158-173, vol. 38, No. 3.
Klein, Barbara K., et al., "Abstract Only: Effects of signal peptide changes on the secretion of bovine somatotropin (bST) from *Escherichia coli*", "Protein Engineering", 1992, pp. 511-517, vol. 5, No. 6.
Kujau, M. J., et al., "Abstract Only: Expression and secretion of functional miniantibodies McPC603scFvDhlx in cell-wall-less L-form . . .", "Applied Microbiology and Biotechnology", 1998, pp. 51-58, vol. 49, No. 1.
Lee, Sang Yup, "Abstract Only: High cell-density culture of *Escherichia coli*", "Trends in Biotechnology", Mar. 1996, pp. 98-105, vol. 14, No. 3.
Lo, Amy C., et al., "Abstract Only: *Bacillus subtilis* beta-1, 4-endoglucanase products from intact and truncated genes are secreted into . . .", "Appl. Environ. Microbiol.", Sep. 1988, pp. 2287-2292, vol. 54, No. 9.
Manoil, C., et al., "Abstract Only: A genetic approach to analyzing membrane protein topology", "Science", 1986, pp. 1403-1408, vol. 233, No. 4771.
Nagahari, K., et al., "Abstract Only: Secretion into the culture medium of a foreign gene product from *Escherichia coli*: use of the ompF . . .", "Embo J.", Dec. 16, 1985, pp. 3589-3592, vol. 4, No. 13A.
Robbens, J., et al., "Abstract Only: Production of soluble and active recombinant murine interleukin-2 in *Escherichia coli* . . .", "Protein Expression and Purification", 1995, pp. 481-486, vol. 6, No. 4.
Toksoy, E., et al., "Abstract Only: High level secretion of TaqI restriction endonuclease by recombinant *Escherichia coli*", "Biotechnology Techniques", Nov. 1999, pp. 803-808, vol. 13, No. 11.

(Continued)

*Primary Examiner* — Maryam Monshipouri
(74) *Attorney, Agent, or Firm* — Kelly K. Reynolds; Steven J. Hultquist; Hultquist IP (57) ABSTRACT

The present invention relates to a method for secreting and producing a target protein into cell culture broth. More particularly, the invention relates to a microorganism co-transformed with a recombinant expression vector containing *E. coli* outer membrane protein F (OmpF) and a recombinant expression vector containing a target protein to be secreted into cell culture broth, as well as a method of secreting and producing the target protein into cell culture broth by culturing the microorganism. According to the invention, the target protein can be secreted into cell culture broth in a pure form without fusion with other proteins so that the efficient isolation and purification of the target protein is possible.

19 Claims, 5 Drawing Sheets

OTHER PUBLICATIONS

Utsumi, Shigeru, et al., "Abstract Only: Signal sequence of preproglycinin affects production of the expressed protein in *Escherichia coli*", "Gene", Nov. 30, 1988, pp. 349-358, vol. 71, No. 2.

Van Der Wal, Fimme J., et al., "Optimization of bacteriocin release protein (BRP)-mediated protein release by *Escherichia coli*: random mutagenesis of . . . ", "Applied and Environmental Microbiology", Feb. 1998, pp. 392-398, vol. 64, No. 2.

Yamamoto, Takeshi, et al., "Expression of chimeric ras protein with OmpF signal peptide in *Escherichia coli*: localization of OmpF fusion protein . . . ", "Appl. Microbiol. Biotechnol.", 1991, pp. 615-621, vol. 35.

FIG. 9 ly complex and very expensive isolation and purification procedures should be carried out. And, the proteins are liable to be exposed to various proteases present in the cytoplasm, which leads to a reduction in yield. Also, in most cases, proteins overexpressed in the cytoplasm are not completely folded and form inactive inclusion bodies. Because these inclusion proteins have no activity as proteins, complex and expensive denaturation and refolding procedures are required to obtain biologically active water-soluble proteins from the inclusion proteins (Choi et al., *Chem. Eng. Sci.*, 66: 876, 2006).

SEQUENCE LISTING

```
<160> NUMBER OF SEQ ID NOS: 6

<210> SEQ ID NO 1
<211> LENGTH: 26
<212> TYPE: DNA
<213> ORGANISM: Artificial
<220> FEATURE:
<223> OTHER INFORMATION: primer

<400> SEQUENCE: 1
cggaattctg gattataccg acgcag                                              26

<210> SEQ ID NO 2
<211> LENGTH: 28
<212> TYPE: DNA
<213> ORGANISM: Artificial
<220> FEATURE:
<223> OTHER INFORMATION: primer

<400> SEQUENCE: 2
gcggatcctt agaactggta aacgatac                                            28

<210> SEQ ID NO 3
<211> LENGTH: 32
<212> TYPE: DNA
<213> ORGANISM: Artificial
<220> FEATURE:
<223> OTHER INFORMATION: primer

<400> SEQUENCE: 3
ggactgcagc acggacacca gaaatgcctg tt                                       32

<210> SEQ ID NO 4
<211> LENGTH: 33
<212> TYPE: DNA
<213> ORGANISM: Artificial
<220> FEATURE:
```

```
<223> OTHER INFORMATION: primer

<400> SEQUENCE: 4
gcgggatcct tattatttca gccccagagc cgg                                    33

<210> SEQ ID NO 5
<211> LENGTH: 32
<212> TYPE: DNA
<213> ORGANISM: Artificial
<220> FEATURE:
<223> OTHER INFORMATION: primer

<400> SEQUENCE: 5
gaactgcagc taatagtgac yctgaatgtc cc                                     32

<210> SEQ ID NO 6
<211> LENGTH: 31
<212> TYPE: DNA
<213> ORGANISM: Artificial
<220> FEATURE:
<223> OTHER INFORMATION: primer

<400> SEQUENCE: 6
gcggatcctt attagcgcag ttcccaccac t                                      31
```

METHOD FOR EXTRACELLULAR PRODUCTION OF TARGET PROTEINS BY CO-EXPRESSION OF OMPF AND TARGET PROTEINS

CROSS-REFERENCE TO RELATED APPLICATIONS

This application is filed under the provisions of 35 USC 371 as the national U.S. stage of International Patent Application PCT/KR2005/002284 filed Jul. 15, 2005. The disclosure of said International Patent Application PCT/KR2005/002284 is hereby incorporated herein by reference in its entirety, for all purposes.

TECHNICAL FIELD

The present invention relates to a method for secreting and producing a target protein into cell culture broth, and more particularly, to a microorganism co-transformed with a recombinant expression vector containing *E. coli* outer membrane protein F (OmpF) and a recombinant expression vector containing a target protein to be secreted into cell culture broth, as well as a method for secreting and producing a target protein into cell culture broth by culturing said microorganism.

BACKGROUND ART

With the development of genetic manipulation, studies on the mass production of useful proteins by the use of bacteria and various animals and plants are frequently being conducted. Up to now, *E. coli* is a host cell mostly frequently used for the mass production of various useful proteins, studies on which are also most frequently conducted (Choi et al., *Chem. Eng. Sci.*, 66: 876, 2006; Lee, *Trends Biotechnol.*, 14:98, 1996). However, if useful proteins to be produced are produced in the cytoplasm of *E. coli*, there are many problems. First, in order for proteins produced in the cytoplasm to be isolated and purified with high purity, considerably complex and very expensive isolation and purification procedures should be carried out. And, the proteins are liable to be exposed to various proteases present in the cytoplasm, which leads to a reduction in yield. Also, in most cases, proteins overexpressed in the cytoplasm are not completely folded and form inactive inclusion bodies. Because these inclusion proteins have no activity as proteins, complex and expensive denaturation and refolding procedures are required to obtain biologically active water-soluble proteins from the inclusion proteins (Choi et al., *Chem. Eng. Sci.*, 66: 876, 2006).

As one of methods to solve such problems, there is a method in which proteins produced in the cytoplasm are secreted into the periplasm or cell culture broth. The extracellular production of a target protein in *E. coli* has various advantages. First, the production of the target protein in *E. coli* cells can fundamentally prevent intracellular proteolysis, so that the stable production of the desired protein can be expected. Second, by the secretion procedure, the correct folding of proteins is possible so as to produce proteins with activity, and the formation of inclusion bodies by incorrect folding can be prevented. Third, by the secretion process, N-terminal secretion signal sequences are removed so that it is possible to maintain the same amino acid sequences as naturally occurring sequences having no N-terminal methionine (Met) residues which are unavoidably linked in intracellular production. Finally, a purification procedure is easily performed. Since there is little or no protein which is naturally secreted from *E. coli* into culture broth, the secretory production of the target protein into cell culture broth allows the target protein to be maintained at high purity, so that the pure isolation of the target protein from the cell culture broth becomes very easy. Although the extracellular production of the target protein in *E. coli* has similar advantages to general secretory production by secretion into the *E. coli* periplasm, the above-described advantages of the extracellular production can be much more effective in terms of industrial production. Because the extracellular secretory production is a method of completely secreting the target protein to the outside of cells, not secreting the target protein into the limited periplasm, it significantly reduces the load in cells resulting from the overexpression of the protein to allow the mass production of proteins by high cell concentration culture and continuous culture. Although both methods allow proteins with high purity to be produced in a purification procedure, the secretory production of the target protein into the periplasm requires a much more complex procedure than the extracellular secretory production, which is not easy to use in industrial applications (Choi and Lee, *Appl. Microbiol. Biotechnol.*, 64:625, 2004). As described above, the advantages of the extracellular secretion are very excellent and diverse and thus various studies on the periplasmic or extracellular secretion of target proteins in *E. coli* have been conducted.

Methods of secreting useful proteins synthesized from *E. coli* into the periplasm or cell culture broth have various advantages in terms of the production of recombinant proteins. First, because the periplasm or culture broth contains a significantly smaller amount of proteins than the cytoplasm does, it is very easy to isolate and purify the desired useful protein with high purity. And, because the useful proteins are separated from the cytoplasm where most of proteases are, intracellular proteolysis can be previously prevented, thus giving good results in terms of yield. Also, because the periplasm is a more oxidized environment than the cytoplasm, disulfide binding is more easily made, so that correct folding of the resulting protein is made, which leads to a remarkable reduction in the formation of inclusion proteins (Choi and Lee, *Appl. Microbiol. Biotechnol.*, 64:625, 2004).

To secrete foreign proteins which are not secreted in *E. coli*, the previously known secretion signal sequences (e.g., OmpA, OmpF, PhoA, SpA, etc.) were linked to the N-terminal end of foreign proteins or linked after some modification (Abrahmsen et al., *EMBO J.*, 4:3901, 1985; Choi and Lee, *Appl. Microbiol. Biotechnol.* 64:625, 2004; Jobling et al., *Plasmid*, 38:158, 1997; Klein et al., *Protein Eng.*, 5:511, 1992; Utsumi et al., *Gene*, 71:349, 1988).

However, such signal sequences or proteins show a great difference in terms of secretion efficiency and have a number of examples where no secretion is occurred. This is because the correlation between signal sequences and target proteins is not yet clearly established and thus studies on the investigation of new signal sequences capable of efficiently secreting target proteins are still being conducted worldwide. Furthermore, although the isolation and purification of the target protein from the periplasm are easier than the isolation and purification from the cytoplasm, the extracellular secretion of the target protein can make the isolation and purification of the target protein easier.

Methods for the extracellular secretion of target proteins in *E. coli*, which have been performed till now, can be broadly divided into the following four categories:

(1) The first method is based on a fusion protein combining a signal peptide and the target protein and mainly uses the signal peptide to secrete target proteins from *E. coli* to the periplasm. Toksoy et al. reported the extracellular production of a TaqI protein by fusion with a maltose binding protein (MBP) (Toksoy et al., *Biotechnol Techniq.*, 3:803, 999). In this case, an *E. coli* XL1 strain was used, and after the induction of expression with 1 mM IPTG, about 270× $10^3$ units/IL culture broth of the TaqI protein was produced in cell culture broth. Lo et al. reported that β-1,4-endoglucanase derived from *Bacillus subtilis* was expressed in *E. coli*, as a result, the extracellular secretion of the protein occurred (Lo et al., *Appl. Environ. Microbiol.*, 54:2287, 1988). Nagahari et al. reported the extracellular secretion of β-endorphin by fusion with the secretion signal sequence and eight N-terminal amino acids of the OmpF protein (Nagahari et al., *EMBO J.*, 4:3589, 1985). In this case, *E. coli* N99, RRI, and MC4100 and their mutants MH1461 (envZ) and MH1160 (ompR) were used as host cells, and among them, the RR1 strain showed the highest secretion efficiency, in which the degradation of β-endorphin occurred by the action of extracellular protease after secretion. The most stable secretion efficiency was shown in the N99 strain. On the other hand, Yamamoto et al. attempted the secretory production of Harvey murine sarcoma virus-derived p21 protein by fusion with the OmpF secretion signal sequence as mentioned above. However, the p21 protein was not secreted to the outside of cells, but accumulated in the cytoplasm in the form of insoluble inclusion bodies (Yamamoto et al., *Appl. Microbiol. Biotechnol.*, 35:615, 1991).

(2) The second method uses the co-production of a target protein and a protein involved in the secretion of the target protein in *E. coli*. Baneyx et al. reported the co-production of a TolAIII protein (*E. coli* transmembrane protein) in the secretory production of an OmpA-TEM-β-lactamase fusion protein (Baneyx and Eugene, *Protein Expr Purif.*, 14:13, 1998). For the secretory production of the OmpA-TEM-β-lactamase fusion protein, a lpp-lac promoter requiring IPTG derivatives was used, and for the expression of the TolAIII protein, a T7lac promoter in need of the IPTG derivatives was used. The expression of the protein in *E. coli* BL21 (DE3) was induced with 1 mM IPTG. As a result, the co-expression with TolAIII showed a 3.5 times increase in the activity of β-lactamase as compared to the single expression of the protein. Robbens et al. reported the co-expression of a kil gene in the production of interleukin-2 (IL-2) (Robbens et al., *Protein Expr Purif.*, 6:481, 1995). In this case, after the IL-2 gene was fused with an OmpA secretion signal sequence, its expression was induced with a tac promoter in need of the IPTG derivatives, and the co-expression of the kil gene used a $P_L$ promoter requiring heat shock at 42° C. It was seen that the IL-2 protein produced in the *E. coli* periplasm before the induction of expression of the kil gene by heat shock was mostly secreted into cell culture broth through the outer membrane after the induction of expression of the kil gene. van der Wal et al. used bacteriocin release protein (BRP) which is an *E. coli* lipoprotein, for the extracellular secretion of β-lactamase (van der Wal et al., *Appl. Environ. Microbiol.*, 64:392, 1998). van der Wal et al. obtained modified BRP genes by the random mutagenesis of the existing BRP gene, and used these modified BRP genes to develop systems which can secrete and produce to the outside of cells in a more stable manner than the existing BRP gene. Aristidou et al. reported that the addition of glycine into medium was effective for increasing secretion efficiency in extracellular secretion with the use of BRP (Aristidou et al., *Biotechnol. Lett.*, 15:331, 1993). As target proteins, α-amylase and β-lactamase were used, and the expression of BRP was induced by a lpp/lac promoter. The α-amylase showed about 10 times higher activity with the addition of 1% glycine into the medium than with the addition of 0.1% glycine. The β-lactamase showed about 2.5 times increase in its activity with the addition of 1.0% glycine.

(3) The third method uses an *E. coli* strain with no outer membrane. This mutant, so called a "L-form", is in a state where the *E. coli* outer membrane was removed so that the cells were formed, having the inner membrane without the periplasm. Namely, the use of a method for secreting proteins to the periplasm, which has been widely used in the prior art, allows the extracellular production of proteins, because once the proteins are passed through the inner cell membrane, they are exposed to cell culture broth without passing through the periplasm. Kujau et al. used a RV308 strain which is L-form *E. coli* strain, for the extracellular secretion of a miniantibody (miniAb) (Kujau et al., *Appl. Microbiol. Biotechnol.*, 49:51, 1998). The miniAb gene was fused with the OmpA secretion signal sequence, after which its expression was induced by the lac promoter. Culturing at a low temperature of 26° C. showed a higher cell concentration and protein production than culturing at 37° C.

(4) The fourth method is to perform extracellular secretion by the fusion of outer membrane protein F (OmpF) with a target protein. In this method, target protein β-endorphin fused with the C-terminal end of the outer membrane protein F was cultured at high cell concentration so as to be secreted to the outside of cells (Korean patent registration No. 10-0447530; Jeong and Lee, *Appl. Environ. Microbiol.*, 68:4979, 2002). However, this method has problems in that high cell concentration culture must be carried out for the extracellular secretion of the target protein, and a step of isolating and purifying the target protein by digestion with various proteases is required because the produced target protein is fused with the OmpF protein.

As described above, although various methods for the extracellular production of a target protein in *E. coli* have been developed, various problems still remain. The above-described methods allow the secretory production of a target protein. However, because most of these methods involve partial lysis of *E. coli*, significant amounts of intracellular proteins of *E. coli* are contained in cell culture broth to reduce the purity of the target protein, thus making it difficult to achieve an easy purification procedure which is the greatest advantage of extracellular secretory production. Also, because these methods involve the lysis of *E. coli*, they have a shortcoming in that high cell concentration culture is difficult so that it also becomes difficult to achive the mass production of the desired protein. Particularly in L-form *E. coli*, only low cell concentration culture is possible because of the structural problem of *E. coli* strains.

DISCLOSURE OF THE INVENTION

Accordingly, the present inventors have made extensive efforts to develop a method for efficiently secreting a target protein from *E. coli* to the outside of the microbial cell (into culture broth), as a result, we found that when *E. coli* outer membrane protein F (OmpF) and a target protein are co-expressed, the target protein can be efficiently secreted from *E. coli* into cell culture broth, and the secreted protein can be isolated and purified in a very simple manner because it is present in a pure form in the cell culture broth, thereby completing the present invention.

Therefore, it is a main object of the present invention to provide a microorganism having a characteristic capable of co-expressing OmpF and a target protein to secrete and produce the target protein to the outside of the microbial cell.

Another object of the present invention is to provide a method for the extracellular secretion and production of a target protein, the method comprising culturing said microorganism.

To achieve the above objects, in one aspect, the present invention provides a recombinant microorganism co-transformed with a recombinant vector containing an OmpF-encoding gene and a recombinant vector containing a target protein-encoding gene and capable of expressing and secreting the target protein to the periplasm of the microorganism, the recombinant microorganism having a characteristic capable of co-expressing the OmpF-encoding gene and the target protein-encoding gene to secrete and produce the target protein to the outside of the microbial cell (into culture broth).

In another aspect, the present invention provides a recombinant microorganism obtained by introducing a recombinant vector containing a target protein-encoding gene and capable of expressing and secreting the target protein to the periplasm of the microorganism, into a microorganism having an OmpF-encoding gene and its promoter introduced into its chromosome so as to be able to express the OmpF-encoding gene, the recombinant microorganism having a characteristic capable of co-expressing the OmpF-encoding gene and the target protein-encoding gene to secrete and produce the target protein to the outside of the microbial cell (into culture broth).

In the present invention, the recombinant vector containing OmpF-encoding gene and the recombinant vector containing the target protein-encoding gene have origins which are expressed in substantially the same conditions. For example, the origin of the recombinant vector containing the OmpF-encoding gene is p15A, and the origin of the recombinant vector containing the target protein-encoding gene is ColE1.

The recombinant vector containing the OmpF-encoding gene has an OmpF promoter in itself, and preferably, the recombinant vector is pACYC-OmpF.

Meanwhile, the recombinant vector containing the target protein-encoding gene preferably has a characteristic capable of expressing and secreting a target protein to the periplasm of a microorganism. When a recombinant microorganism co-transformed with the recombinant vector having this characteristic and the OmpF-encoding gene is cultured, the target protein can be secreted into cell culture broth.

Accordingly, the present invention also provides a method for the extracellular secretion and production of a target protein, the method comprising the steps of: (a) culturing said recombinant microorganism to secrete the target protein to the outside of the microbial cell (into culture broth); and (b) collecting the target protein from the culture broth.

In still another aspect, the present invention provides a recombinant vector constructed by introducing an OmpF-encoding gene into a vector containing a target protein-encoding gene and capable of expressing and secreting the target protein to the periplasm of a microorganism, the recombinant vector having a characteristic capable of co-expressing the OmpF-encoding gene and the target protein-encoding gene to secrete the target protein to the outside of the microbial cell (into culture broth).

In yet another aspect, the present invention provides a method for the extracellular secretion and production of a target protein, the method comprising the steps of: (a) culturing the microorganism transformed with said recombinant vector and the transformed microorganism to secrete the target protein to the outside of the microbial cell (into culture broth); and (b) recovering the target protein from the culture broth.

In the inventive method for the extracellular secretion and production of the target protein, the extracellular secretion of the target protein in the step (a) dose not accompany the lysis of the microorganism.

Hereinafter, the present invention will be described in more detail.

For the co-expression of E. coli OmpF, the present inventors constructed recombinant plasmid vector pACYC-OmpF. This recombinant plasmid contains an E. coli OmpF gene and promoter and a chloramphenicol-resistant gene and has a p15A origin so that it is easily co-expressed with a ColE1 origin which is used in most of expression vectors. The OmpF gene and promoter were obtained from an E. coli BL21 (DE3) chromosome by PCR.

Then, in order to prepare a transformed E. coli strain which secretes a target protein to the outside of the microbial cell, various recombinant plasmids were used. First, E. coli alkaline phosphatase was used as a target protein. The alkaline phosphatase consists of 450 amino acids and has a molecular weight of about 50 kDa. This protein is known to be expressed in E. coli and secreted to the periplasm and also to have enzymatic activity only when it is present in the periplasm (Manoil et al., Science, 233:1403, 1986). The recombinant plasmid pTrcS1PhoA capable of secreting and producing alkaline phosphatase to the periplasm and the plasmid pACYC-OmpF were co-transformed and cultured in E. coli, and the culture broth was analyzed and the results showed that the target protein alkaline phosphatase was secreted from E. coli BL21(DE3) and MC4100 into the culture broth with very good efficiency. Pure alkaline phosphatase secreted from the above E. coli strains to the outside of the microbial cell could be obtained. Also, other proteins in addition to alkaline phosphatase, i.e., an epithelial cell growth factor (EGF) consisting of 53 amino acids, human leptin protein, an endoxylanase from Bacillus sp., were used as target proteins to be analyzed for their secretion into culture broth. It was shown that all the above-described proteins were efficiently secreted from transgenic E. coli into culture broth.

DETAILED DESCRIPTION OF THE INVENTION

Hereinafter, the present invention will be described in detail by examples. However, it will be obvious to a person skilled in the art that these examples are given for a better understanding of the present invention and not construed to limit the scope of the present invention.

Particularly, the following examples illustrated culturing a microorganism co-transformed with a recombinant vector containing an OmpF-encoding gene and a recombinant vector containing a target protein-encoding gene so as to secrete and produce the target protein to the outside of the microbial cell (into culture broth). However, it will be obvious to a person skilled in the art that the use of a microorganism transformed with a recombinant vector constructed by introducing an OmpF-encoding gene into a vector containing a target protein-encoding gene and capable of expressing and secreting the target protein to the periplasm of the microorganism also allows the target protein to be secreted and produced to the outside of the microbial cell (into culture broth). In addition to the recombinant vector containing the OmpF-encoding gene, it will be obvious to a person skilled in the art that the use of a recombinant microorganism constructed by introducing a recombinant vector containing a target protein-encoding gene and capable of expressing and secreting the target protein to the periplasm of the microorganism, into a recombinant microorganism having the OmpF-encoding gene and its promoter introduced into its chromosome so as to be able to express the OmpF-encoding gene, allows the target protein to be secreted and produced to the outside of the microbial cell (into culture broth).

Furthermore, the following examples illustrated pJS101ΔP (a recombinant vector capable of expressing and secreting endoxylanase to the periplasm) and pTrcKObD (a recombinant vector capable of expressing and secreting a leptin protein to the periplasm of *E. coli*) as the recombinant vectors containing a target protein-encoding gene and capable of expressing and secreting the target protein to the periplasm of *E. coli*. However, it will be obvious to a person skilled in the art that any recombinant vector may be used without limitations if it is a recombinant vector capable of expressing and secreting the target protein to the periplasm of a microorganism. In addition, although the following examples illustrated only alkaline phosphatase, an EGF, endoxylanase and leptin, as target proteins, it will be appreciated by a person skilled in the art that the scope of the present invention is not limited to the illustrated target proteins.

EXAMPLE 1

Development of OmpF Gene Expression System

Figure 1:
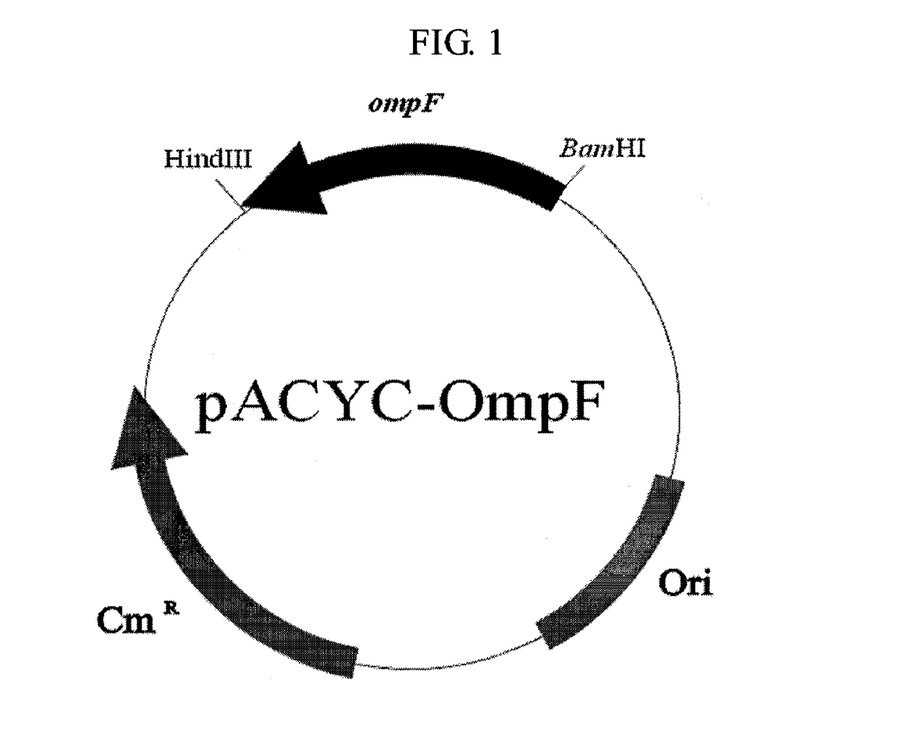
FIG. 1 is a gene map of plasmid pACYC-OmpF.

A chromosome was isolated from *E. coli* BL21(DE3), and then, to clone an ompF gene and its promoter region, primer 1 of SEQ ID NO: 1 (5'-CGGAATTCTGGATTATAC-CGACGCAG-3') and primer 2 of SEQ ID NO: 2 (5'-GCG-GATCCTTAGAACTGGTAAACGATAC-3') were synthesized. The chromosome was subjected to PCR using the primers 1 and 2 to obtain a 2160-bp PCR product. The PCR product was digested with HidIII and BamHI and cloned into pACYC184 (New England Biolabsd, USA). The cloned plasmid was transformed into *E. coli* XL1-Blue [supE44 hsdR17 recA1 endA1 gyrA96 thi relA1 lacF'(proAB$^+$ lacI$^q$ lacZ ΔM15 Tn(tet$^r$))] to obtain recombinant plasmid pACYC-OmpF (FIG. 1).

EXAMPLE 2

Construction of Recombinant Plasmid pTrcS1Phoa

A chromosome was isolated from *E. coli* W3110 (derived from *E. coli* K-12, λ$^-$, F$^-$, prototrophic), and then, to obtain an alkaline phosphatase gene, primer 3 of SEQ ID NO: 3 (5'-GGACTGCAGCACGGACACCAGAAATGCCTGTT-3') and primer 4 of SEQ ID NO: 4 (5'-GCGGGATCCTTAT-TATTTCAGCCCCAGAGCCGG-3') were synthesized. The chromosome was subjected to PCR using the primers 3 and 4. The PCR reaction was performed under the following conditions: pre-denaturation at 94° C. for 5 min; 30 cycles of denaturation at 94° C. for 45 sec, annealing at 52° C. for 45 sec, and extension at 72° C. for 1 min and 10 sec; and then, final extension at 72° C. for 7 min. The DNA fragment obtained by the PCR reaction was electrophoresed on agarose gel to isolate about 1360 bp DNA fragment. The isolated DNA fragment was digested with two restriction enzymes PstI and BamHI. Meanwhile, recombinant plasmid pJS101ΔP (Choi, J. H., et al., *Appl. Microbiol. Biotechnol.*, 53:640, 2000) was digested with two restriction enzymes PstI and BamHI to remove an endoxylase gene, and the resulting plasmid was mixed and ligated with the above-obtained DNA fragment using T4 DNA ligase, thus obtaining recombinant plasmid pTrcS1PhoA.

EXAMPLE 3

Extracellular Production of Alkaline Phosphatase

Figure 2:
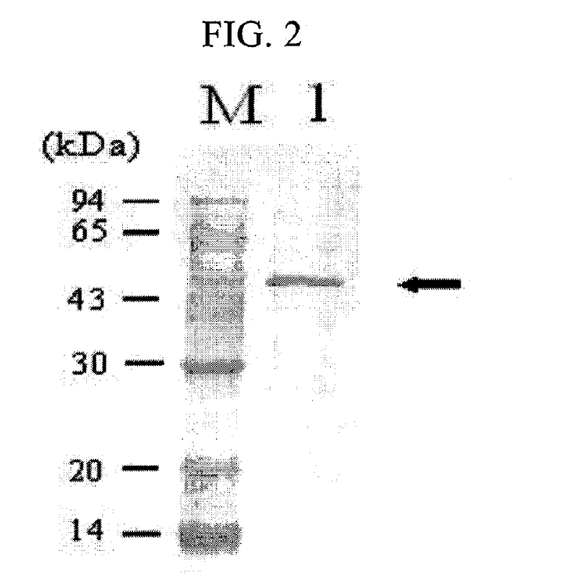
FIG. 2 shows the results of SDS-PAGE gel analysis for a culture of E. coli BL21(DE3) co-transformed with plasmids pACYC-OmpF and pTrcS1PhoA.

An *E. coli* BL21(DE3) strain was co-transformed with recombinant plasmids pACYC-OmpF and pTrcS1PhoA. The transformation was performed by electroporation, and the transformation strain was selected from an LB plate medium containing antibiotic ampicillin (50 μg/L) and chloramphenicol (34 μg/L). The transformed strain was inoculated into LB liquid medium (10 g/L tryptone, 5 g/L yeast extract, 5 g/L NaCl) and cultured at 30° C., and then, examined for the extracellular secretion of alkaline phosphatase. When the optical density (O.D.) measured at a wavelength of 600 nm with a spectrophotometer after inoculation into the liquid medium reached 0.7, each of 0.1 and 1.0 mM of IPTG was added to the culture medium to induce the gene expression. 12 hours after the induction of gene expression, 1 mL of each culture broth was collected and measured for alkaline phosphatase activity, at the same time, analyzed on SDS-PAGE gel (FIG. 2). In FIG. 2, "M" represents the molecular weight standard of protein, and "1" represents the results of SDS-PAGE gel analysis for the culture of BL21(DE3) transformed with pACYC-OmpF and pTrcS1PhoA, 12 hours after the induction of expression with 0.1 mM IPTG. As shown in FIG. 2, an alkaline phosphatase corresponding to about 50 kDa could be detected, indicating that the above system can secrete the target protein into the culture broth very efficiently. Namely, it could be seen that the secretion of alkaline phosphatase in *E. coli* occurred. The amount of the secreted alkaline phosphatase was quantified by the Bradford method, and the result showed that about 0.1 g/L of alkaline phosphatase was produced in a water-soluble form in the culture broth.

Figure 3:
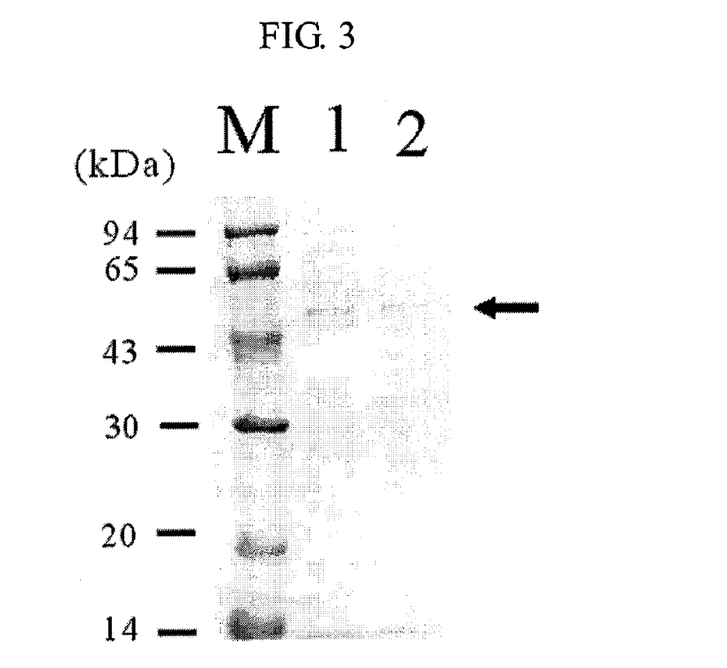
FIG. 3 shows the results of SDS-PAGE gel analysis for a culture of E. coli MC4100 co-transformed with plasmids pACYC-OmpF and pTrcS1PhoA.

As described above, it was seen that the alkaline phosphatase was efficiently secreted from *E. coli* BL21(DE3) into the culture broth, and also, this protein was secreted from other *E. coli* strains in addition to *E. coli* BL21(DE3) into culture broth. The above-described recombinant plasmids pACYC-OmpF and pTrcS1PhoA were co-transformed into *E. coli* MC4100 [F⁻ araD 139 Δ(argF⁻lac)U169 rpsL150(str$^r$) relA1 flbB5301 deoC1 ptsF25 rbsR]. The transformation was performed by electroporation, and the transformation strain was selected from an LB plate medium containing antibiotic ampicillin (50 μg/L) and chloramphenicol (34 μg/L). The transformed strain was inoculated into LB liquid medium (10 g/L tryptone, 5 g/L yeast extract, and 5 g/L NaCl), and cultured in the medium at 30° C. and examined for the extracellular secretion of alkaline phosphatase. When the optical density (O.D.) measured at a wavelength of 600 nm with a spectrophotometer after inoculation into the liquid medium reached 0.7, each of 0.1 and 1.0 mM of IPTG was added to the culture medium to induce the gene expression. 12 hours after the induction of gene expression, 1 mL of each culture was collected and analyzed on SDS-PAGE gel (FIG. 3). In FIG. 3, "M" represents molecular weight standard of protein, "1" represents the results of SDS-PAGE gel analysis for the culture of *E. coli* MC4100 transformed with pACYC-OmpF and pTrcS1PhoA, 12 hours after the induction of gene expression with 1 mM IPTG, and "2" represents the results of SDS-PAGE gel analysis for the culture of *E. coli* MC4100 transformed with pACYC-OmpF and pTrcS1PhoA, 12 hours after the induction of expression with 0.1 mM IPTG As shown in FIG. 3, an alkaline phosphatase corresponding to about 50 kDa could be detected, indicating that the above system can secrete the target protein into the culture broth very efficiently. However, the secretion efficiency of alkaline phosphatase in *E. coli* MC4100 was lower than that in *E. coli* BL21(DE3).

EXAMPLE 4

Activity Measurement of Alkaline Phosphatase Secreted from Recombinant *E. Coli*

The activity of alkaline phosphatase was measured in the following manner (Brickman and Beckwith, *J. Mol. Biol.,* 96:307, 1975). Recombinant *E. coli* strain BL21(DE3) co-transformed with recombinant plasmids pACYC-OmpF and pTrcS1PhoA was inoculated into a 250 mL flask containing 50 mL LB medium and cultured at 37° C. When the optical density (O.D.) measured at a wavelength of 600 nm with a spectrophotometer reached 0.7, 1 mM IPTG was added to the culture medium to induce the gene expression. 12 hours after the induction of gene expression, 1 mL of the culture was collected, to which 0.1 mL chlroform was added. Then, the mixture was allowed to react at 37° C. for 5 minutes. After the reaction, 0.1 mL of 0.4% PNPP (p-nitrophenyl phosphate) was added to the reaction mixture, followed by reaction at 37° C. for 5 minutes. After the reaction, 0.1 mL of 1M $K_2HPO_4$ solution was added to the reaction mixture to stop the reaction. The obtained reaction solution was suitably diluted with 50 mM Tris-HCl solution and measured for absorbencies at two wavelengths of 420 nm and 550 nm. Also, in control tests, *E. coli* BL21(DE3) with no plasmid and a culture of *E. coli* BL21(DE3) transformed with pTrcS1PhoA were measured for alkaline phosphatase activity in the same manner as described above. The alkaline phosphatase activity was calculated according to the following equation, and the results are shown in Table 1 below:

$$\text{Activity (U/mL)} = 1000 \times (AbS_{420nm} - 1.75 \times AbS_{550nm}) / [\text{reaction time (min)} \times \text{reaction volume (mL)}]$$

TABLE 1

Alkaline phosphatase activities in recombinant *E. coli* strains with various conditions

| Recombinant *E. coli* | Alkaline phosphatase activities (U/mL) |
|---|---|
| *E. coli* BL21(DE3) | Not detected |
| *E. coli* BL21(DE3) (pTrcS1PhoA), 0.1 mM induction | Not detected |
| *E. coli* BL21(DE3) (pTrcS1PhoA, pACYC-OmpF), 0.1 mM induction | 7500 |
| *E. coli* BL21(DE3) (pTrcS1PhoA, pACYC-OmpF), 0.01 mM induction | 7800 |

As shown in Table 1, the cultures of *E. coli* strains transformed with plasmids pACYC-OmpF and pTrcS1PhoA showed high alkaline phosphatase activities, whereas the non-transformed *E. coli* strains showed little or no activity. Alkaline phosphatase has no activity in cells and thus it shows activity only when disulfide binding occurs in the periplasm by a secretion procedure. In view of the above test results, it can be seen that alkaline phosphatase produced in the transformed recombinant *E. coli* strains was successively secreted into the culture broth with very high efficiencies.

EXAMPLE 5

Effect Of NaCl Concentration On Extracellular Secretion Of Alkaline Phosphatase

Figure 4:
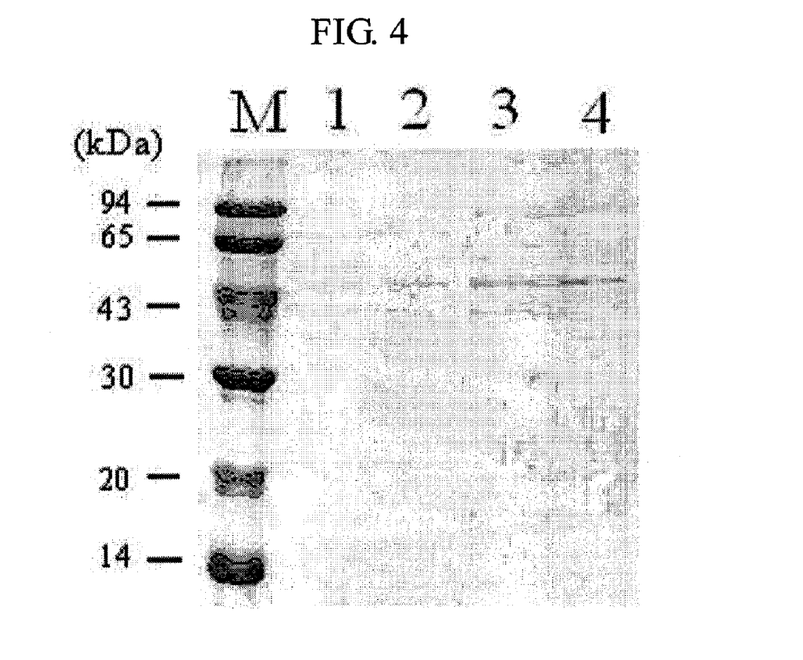
FIG. 4 shows the results of SDS-PAGE gel analysis for cultures obtained by culturing E. coli BL21(DE3) transformed with plasmids pACYC-OmpF and pTrcS1PhoA, at various NaCl concentrations.

*E. coli* BL21(DE3) strain was co-transformed with recombinant plasmids pACYC-OmpF and pTrcS1PhoA. The transformation was performed by electroporation, and the transformation strain was selected from an LB plate medium containing antibiotic ampicillin (50 μg/L) and chloramphenicol (34 μg/L). The transformed strain was inoculated into LB liquid medium (10 g/L tryptone, 5 g/L yeast extract, and 0, 1, 5 and 10 g/L NaCl) with various NaCl concentrations, and cultured at 30° C., and then examined for the extracellular secretion of alkaline phosphatase. The optical density (O.D.) measured at a wavelength of 600 nm with a spectrophotometer after inoculation into the liquid medium reached 0.7, each of 0.1 and 1.0 mM of IPTG was added to the culture broth to induce the gene expression. 12 hours after the induction of gene expression, 1 mL of each culture broth was collected and analyzed on SDS-PAGE gel (FIG. 4). In FIG. 4, "M" represents molecular weight standard of protein, "1" to "4" represent the results of SDS-PAGE gel analysis for the culture broth of *E. coli* BL21(DE3) transformed with pACYC-OmpF and pTrcS1PhoA, 12 hours after the induction of expression with 0.1 mM IPTG Namely, the lines 1-4 show results for samples obtained after culturing in LB liquid media (10 g/L tryptone, 5 g/L yeast extract, and 0, 1, 5 and 10 g/L NaCl) with various NaCl concentrations, respectively. As shown in FIG. 4, an alkaline phosphatase protein corresponding to about 50 kDa could be detected. Particularly, it could be seen that the secretion of alkaline phosphatase into the culture broth increased as the NaCl concentration increased from 0 to 10 g/L.

EXAMPLE 6

Construction of Recombinant Plasmid PsEGF

Figure 5:
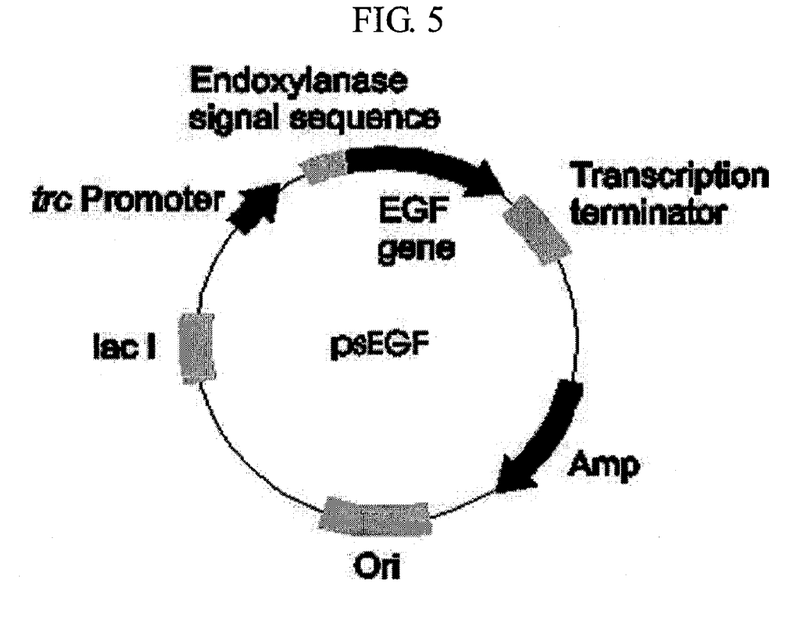
FIG. 5 is a gene map of plasmid psEGF.

Using a recombinant plasmid G82, inserted with an epithelial cell growth factor (EGF) gene, provided by Korea Cytokine Bank(Department of Life Science, Jeonbuk University, Jeonju-si, Jeollabuk-do), as a template DNA to obtain an EGF gene, primer 5 of SEQ ID NO: 5 (5'-GAACTG-CAGCTAATAGTGACYCTGAATGTCCC-3') and primer 6 of SEQ ID NO: 6 (5'-GCGGATCCTTATTAGCGCAGTTC-CCACCACT-3') were synthesized and used for PCR. The PCR reaction was performed under the following conditions: pre-denaturation at 94° C. for 5 min; 30 cycles of denaturation at 94° C. for 45 sec, annealing at 56° C. for 45 sec, and extension at 72° C. for 30 sec; and then, final extension at 72° C. for 7 min. The DNA fragment obtained by the PCR reaction was electrophoresed on agarose gel to isolate amplified EGF DNA fragment. The isolated DNA fragment was digested with two restriction enzymes PstI and BamHI. At the same time, the recombinant plasmid pJS101ΔP (Choi, J. H., et al., *Appl. Microbiol. Biotechnol.*, 53:640, 2000) was digested with two restriction enzymes PstI and BamHI to remove an endoxylase gene, and the resulting plasmid was mixed and ligated with the above-obtained DNA fragment using T4 DNA ligase, thus obtaining recombinant plasmid psEGF (FIG. 5).

EXAMPLE 7

Extracellular Secretion and Production of EGF

Figure 6:
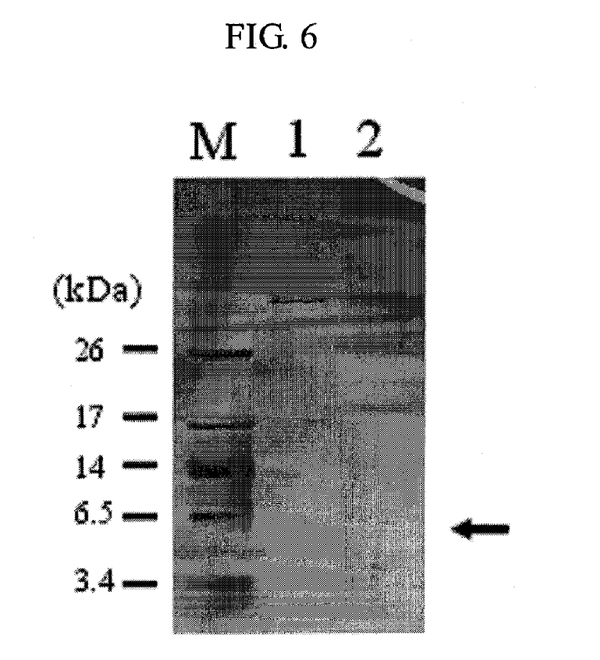
FIG. 6 shows the results of SDS-PAGE gel analysis for a culture of E. coli BL21(DE3) co-transformed with plasmids pACYC-OmpF and psEGF.

An *E. coli* BL21(DE3) strain was co-transformed with recombinant plasmids pACYC-OmpF and psEGF. The transformation was performed by electroporation, and the transformation strain was selected from an LB plate medium containing antibiotic ampicillin (50 μg/L) and chloramphenicol (34 μg/L). The transformed strain was inoculated into LB liquid medium (10 g/L tryptone, 5 g/L yeast extract, 5 g/L NaCl) and examined for the extracellular secretion of an EGF. When the optical density (O.D.) measured at a wavelength of 600 nm with a spectrophotometer after inoculation into the liquid medium reached 0.7, each of 0.1 and 1.0 mM of IPTG was added to the culture medium to induce gene expression. 12 hours after the induction of gene expression, 1 mL of culture was collected and analyzed on Tricine SDS-PAGE (Shagger, H. and von Jogot, G., *Anal. Biochem.*, 166:368, 1987) gel. The result of staining with general staining method after SDS-PAGE is shown in FIG. 6. In FIG. 6, "M" represents the standard molecular weight of protein, and "1" represents the results of SDS-PAGE gel analysis for the culture of BL21(DE3) transformed with pACYC-OmpF and psEGF, 12 hours after the induction of expression with 0.1 mM IPTG, and "2" represents the results of SDS-PAGE gel analysis for the culture of BL21(DE3) transformed with pACYC-OmpF and psEGF, 12 hours after the induction of expression with 1 mM IPTG. As shown in FIG. 6, about 36 kDa of outer membrane protein F, together with an EGF protein (arrowed) corresponding to about 5 kDa could be detected by SDS-PAGE. Also, a little amount of cells were detected to be lysed at 1 mM of IPTG concentration, and cells were detected not to be lysed without the decrease of expression rate at 0.1 mM of IPTG concentration but because of protein property, were detected not to be stained as blue.

Figure 7:
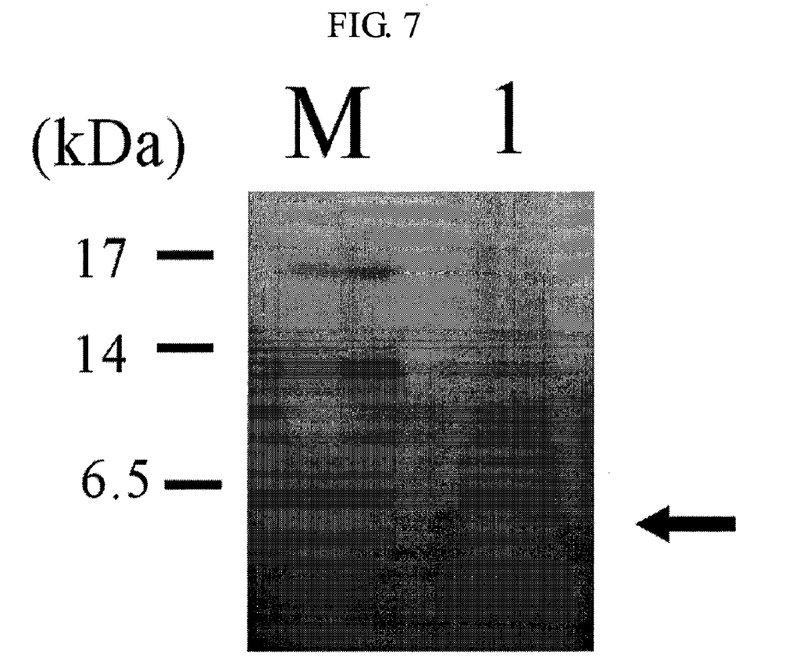
FIG. 7 shows the results of SDS-PAGE gel analysis for a $CuCl_2$-stained culture of E. coli BL21(DE3) co-transformed with plasmids pACYC-OmpF and psEGF.

Hence, instead of staining with commonly used coomassie blue method, after being stained with 300 mM CuCl₂ solution for 5 minutes (Lee, C. et al., *Anal. Biochem.*, 166:308, 1987), the same sample was examined again (FIG. 7). In FIG. 7, "M" represents the standard molecular weight of protein, and "1" represents the results of SDS-PAGE gel analysis for the culture of BL21(DE3) transformed with pACYC-OmpF and psEGF, 12 hours after the induction of expression with 0.1 mM IPTG. As shown in FIG. 7, it could be detected that an EGF protein (arrowed) was efficiently secreted into the culture. Namely, it could be seen that the secretion of EGF protein occurred in *E. coli*. The amount of the secreted EGF protein was quantified by the Bradford method, and the result showed that about 0.07 g/L of EGF protein was produced in the culture broth in a water-soluble form.

EXAMPLE 8

Extracellular Secretion and Production of Endoxylanase

Figure 8:
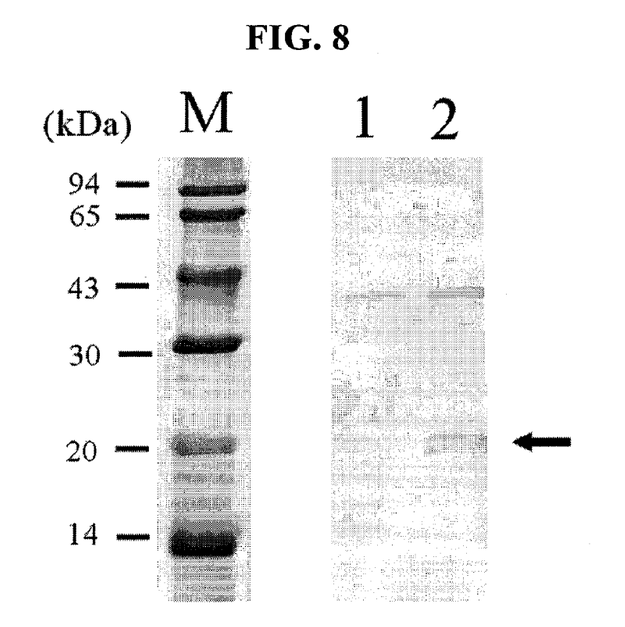
FIG. 8 shows the results of SDS-PAGE gel analysis for a culture of E. coli BL21(DE3) co-transformed with plasmids pACYC-OmpF and pJS101ΔP.

Recombinant plasmid pJS101ΔP is a recombinant vector capable of expressing and secreting an endoxylanase from *Bacillus* sp. to the periplasm (Choi, J. H., et al., *Appl. Microbiol. Biotechnol.*, 53:640, 2000). *E. coli* BL21(DE3) strain was co-transformed with recombinant plasmids pACYC-OmpF and pJS101ΔP to secrete and produce endoxylanase from *E. coli* into culture broth. The transformation was performed by electroporation, and the transformation strain was selected from an LB plate medium containing antibiotic ampicillin (50 μg/L) and chloramphenicol (34 μg/L). The transformed strain was inoculated into LB liquid medium (10 g/L tryptone, 5 g/L yeast extract, and 5 g/L NaCl), and cultured in the medium at 30° C. and examined for the extracellular secretion of endoxylanase. When the optical density (O.D.) measured at a wavelength of 600 nm with a spectrophotometer after inoculation into the liquid medium reached 0.7, 0.1 mM of IPTG was added to the culture medium to induce gene expression. 12 hours after the induction of gene expression, 1 mL of culture was collected and analyzed on SDS-PAGE gel. Then it was stained with general staining method after SDS-PAGE (FIG. 8). In FIG. 8, "M" represents the standard molecular weight of protein, and "1" represents the results of SDS-PAGE gel analysis for the culture of BL21(DE3) transformed with only pACYC-OmpF, 12 hours after the induction of expression with 0.1 mM IPTG and "2" represents the results of SDS-PAGE gel analysis for the culture of BL21(DE3) transformed with pACYC-OmpF and pJS101ΔP, 12 hours after the induction of expression with 0.1 mM IPTG. As shown in FIG. 7, about 36 kDa of outer membrane protein F, together with an endoxylanase (arrowed) corresponding to about 20 kDa could be detected by SDS-PAGE. The result indicates that the endoxylanase protein in *E. coli* was efficiently secreted into the culture broth during culturing.

EXAMPLE 9

Extracellular Secretion and Production of a Human Leptin Protein

Figure 9:
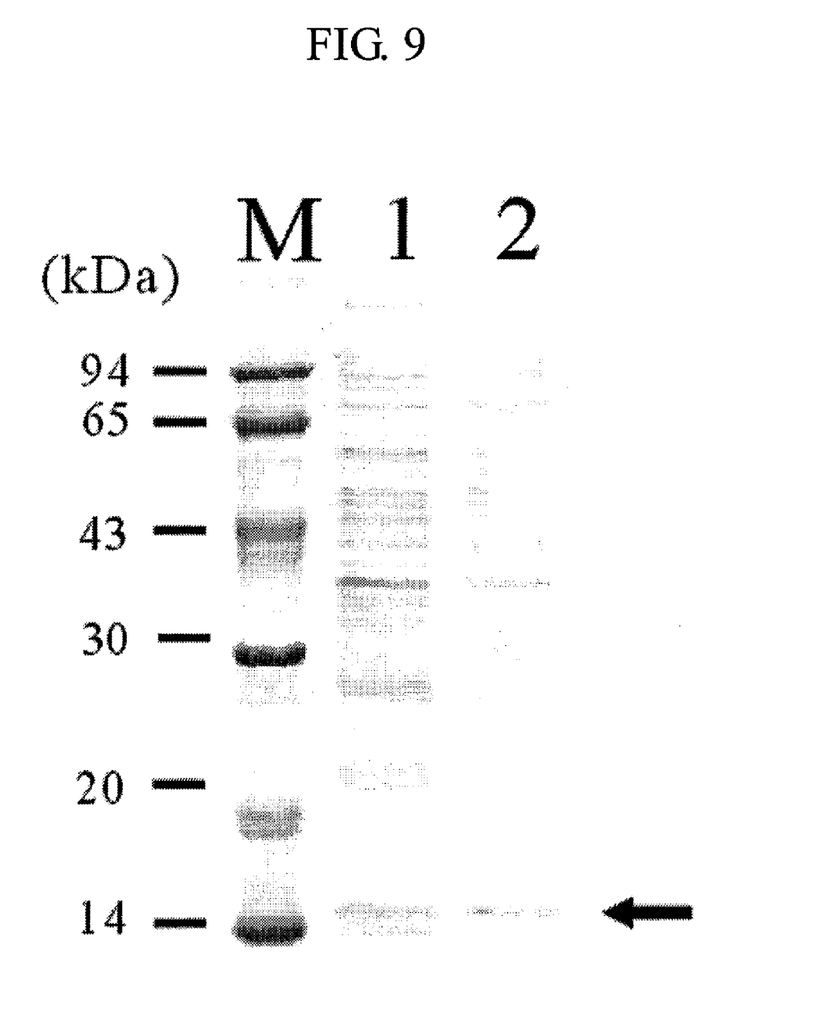
FIG. 9 shows the results of SDS-PAGE gel analysis for a culture of *E. coli* BL21(DE3) co-transformed with plasmids pACYC-OmpF and pTrcKObD.

Recombinant plasmid pTrcKObD is a recombinant vector capable of expressing and secreting a human leptin protein to the periplasm of *E. coli* (Jeong, K. J. and Lee, S. Y., *Biotechnol. Bioeng.*, 67:398, 2000). *E. coli* BL21(DE3) strain was co-transformed with recombinant plasmids pACYC-OmpF and pTrcKObD to secrete and produce a human leptin protein from *E. coli* into culture broth. The transformation was performed by electroporation, and the transformation strain was selected from an LB plate medium containing antibiotic ampicillin (50 μg/L) and chloramphenicol (34 μg/L). The transformed strain was inoculated into LB liquid medium (10 g/L tryptone, 5 g/L yeast extract, and 5 g/L NaCl), and cultured in the medium at 30° C. and examined for the extracellular secretion of leptin protein. When the optical density (O.D.) measured at a wavelength of 600 nm with a spectrophotometer after inoculation into the liquid medium reached 0.7, each of 0.1 and 1.0 mM of IPTG was added to the culture medium to induce gene expression. 12 hours after the induction of gene expression, 1 mL of culture was collected and analyzed on SDS-PAGE gel. Then it was stained with general staining method after SDS-PAGE (FIG. 9). In FIG. 9, "M" represents the standard molecular weight of protein, and "1" represents the results of SDS-PAGE gel analysis for the culture of BL21(DE3) transformed with pACYC-OmpF and pTrcKObD, 12 hours after the induction of expression with 1 mM IPTG, and "2" represents the results of SDS-PAGE gel analysis for the culture of BL21(DE3) transformed with pACYC-OmpF and pTrcKObD, 12 hours after the induction of expression with 0.1 mM IPTG. As shown in FIG. 9, about 36 kDa of outer membrane protein F, together with a leptin protein (arrowed) corresponding to about 14 kDa could be detected by SDS-PAGE. Also, a little amount of cells were detected to be lysed when the expression was induced with 1 mM of IPTG concentration, and cells were detected not to be lysed without the decrease of expression rate when the expression was induced with 0.1 mM of IPTG concentration. The result indicates that the leptin protein in *E. coli* was efficiently secreted into the culture broth during culturing.

As described above, specific parts of the present invention have been explained fully, however, it will be apparent to those skilled in the art that such specific technologies correspond merely to preferred embodiments and the scope of the present invention will not be limited by those embodiments. Accordingly, the practical scope of the present invention will be defined by the appended claims and equivalents thereof.

INDUSTRIAL APPLICABILITY

As described and demonstrated in detail above, the present invention provides the microorganism that secretes the target protein into the cell culture broth, as well as the method for secreating and producing the target protein to the outside of the microbial cells. Although when methods according to the prior art are used to secrete a recombinant protein from *E. coli* into cell culture broth, the desired protein can be secreted and produced to the outside of the microbial cell, most of the prior methods involve some lysis of *E. coli*, so that no small amount of intracellular proteins of *E. coli* is contained in the culture broth to reduce the purity of the target protein, thus making a purification process difficult. On the contrary, in the present invention, cells grow by constitutive expression using the OmpF promoter at the same time, the target protein is expressed. Thus, the secretion of the target protein increases in proportion to an increase in cell concentration, at the same time, the target protein is produced with high purity in a very efficient manner. Also, the inventive method is much simpler than the prior art. Accordingly, by the present invention, various target protein can be secreted and produced into cell culture broth using the inventive microorganism.

What is claimed is:

1. A recombinant microorganism co-transformed with:
   a first recombinant vector containing a gene encoding OmpF; and
   a second recombinant vector containing a gene encoding a target protein, wherein upon expression, the target protein is secreted into the periplasm of the microorganism, wherein the recombinant microorganism is capable of co-expressing the gene encoding OmpF and the gene encoding the target protein and wherein the target protein is secreted extracellularly to the microbial cell into a culture broth in which the cell is present.

2. A recombinant microorganism obtained by:
   introducing a recombinant vector containing a gene encoding a target protein, wherein upon expression, the target protein is secreted into the periplasm of the microorganism, into a recombinant microorganism having a gene encoding OmpF and its promoter such that the microorganism is capable of expressing the gene encoding OmpF,
   wherein the recombinant microorganism is capable of co-expressing the gene encoding OmpF and the gene encoding the target protein and wherein the target protein is secreted extracellularly to the microbial cell into a culture broth in which the cell is present.

3. The recombinant microorganism according to claim 1, wherein the recombinant vector containing a gene encoding OmpF and the recombinant vector containing a gene encoding a target protein have origins of replication which are expressed in substantially the same conditions.

4. The recombinant microorganism according to claim 1, wherein the origin of replication of the recombinant vector containing the gene encoding OmpF is p15A, and the origin of replication of the recombinant vector containing the gene encoding a target protein is ColE1.

5. The recombinant microorganism according to claim 1, wherein the recombinant vector containing the gene encoding OmpF comprises an OmpF promoter.

6. The recombinant microorganism according to claim 1, wherein the recombinant vector containing the gene encoding OmpF is pACYC-OmpF.

7. The recombinant microorganism according to claim 1, wherein the gene encoding OmpF is from *E. coli*.

8. The recombinant microorganism according to claim 1, wherein the recombinant microorganism is *E. coli*.

9. A method for the extracellular production of a target protein, the method comprising the steps of:
   (a) culturing the recombinant microorganism according to claim 1, to secrete the target protein extracellularly to the microbial cell, into a culture broth in which the cell is present; and
   (b) recovering the target protein from the culture broth.

10. The method for the extracellular production of a target protein according to claim 9, wherein the extracellular secretion of the target protein in step (a) does not accompany the lysis of the microorganism.

11. A recombinant vector constructed by introducing a gene encoding OmpF into a vector containing a gene encoding a target protein and capable of expressing and secreting the target protein into the periplasm of a microorganism, wherein the recombinant vector is capable of independently co-expressing the gene encoding OmpF and the gene encoding the target protein to secrete the target protein extracellularly to the microbial cell, into a culture broth in which the cell is present.

12. The recombinant vector according to claim 11, the gene encoding OmpF is from *E. coli*.

13. A microorganism transformed with the recombinant vector of claim 11.

14. The transformed microorganism according to claim 13, wherein the microorganism is *E. coli*.

15. A method for the extracellular production of a target protein, the method comprising the steps of:

(a) culturing the transformed microorganism according to claim 13, to secrete the target protein extracellularly to the microbial cell, into a culture broth in which the cell is present; and (b) recovering the target protein from the culture broth.

16. The method for the extracellular production of a target protein according to claim 15, wherein the extracellular secretion of the target protein in step (a) does not accompany the lysis of the microorganism.

17. The recombinant microorganism according to claim 2, wherein the gene encoding OmpF is from *E. coli*.

18. The recombinant microorganism according to claim 2, wherein the recombinant microorganism is *E. coli*.

19. A method for the extracellular production of a target protein, the method comprising the steps of:

(a) culturing the recombinant microorganism according to claim 2, to secrete the target protein extracellularly to the microbial cell, into a culture broth in which the cell is present; and (b) recovering the target protein from the culture broth.

\* \* \* \* \*